United States Patent [19]

Hassler

[11] Patent Number: 4,957,099
[45] Date of Patent: Sep. 18, 1990

[54] SHOCK WAVE SOURCE FOR EXTRACORPOREAL LITHOTRIPSY

[75] Inventor: Dietrich Hassler, Uttenreuth, Fed. Rep. of Germany

[73] Assignee: Siemens Aktiengesellschaft, Berlin and Munich, Fed. Rep. of Germany

[21] Appl. No.: 296,077

[22] Filed: Jan. 12, 1989

[30] Foreign Application Priority Data

Feb. 10, 1988 [DE] Fed. Rep. of Germany ....... 3804096

[51] Int. Cl.⁵ .............................................. A61B 17/22
[52] U.S. Cl. .............................. 128/24 A; 128/660.03
[58] Field of Search ........... 128/24 A, 660.03, 660.01, 128/328, 661.01, 24 EL; 606/128

[56] References Cited

U.S. PATENT DOCUMENTS

| | | |
|---|---|---|
| 3,990,300 | 11/1976 | Kossoff . |
| 4,315,514 | 2/1982 | Drewes et al. ................. 128/24 A |
| 4,526,168 | 7/1985 | Hassler et al. . |
| 4,617,931 | 10/1986 | Dory .............................. 128/328 |
| 4,633,308 | 12/1986 | Dukes et al. ................. 128/661.01 |
| 4,646,756 | 3/1987 | Watmough et al. .............. 128/804 |
| 4,787,394 | 11/1988 | Ogura ........................... 128/660.03 |
| 4,836,191 | 6/1989 | Noske et al. .................... 128/24 A |
| 4,865,042 | 9/1989 | Umemura et al. ............ 128/660.03 |
| 4,875,487 | 10/1989 | Seppi ........................... 128/660.03 |

FOREIGN PATENT DOCUMENTS

| | | | |
|---|---|---|---|
| 0280088 | 8/1988 | European Pat. Off. ........... 128/328 |
| 3736733 | 5/1988 | Fed. Rep. of Germany ...... 128/328 |
| 2140693 | 12/1984 | United Kingdom . |

*Primary Examiner*—Ruth S. Smith
*Assistant Examiner*—John D. Zele
*Attorney, Agent, or Firm*—Hill, Van Santen, Steadman & Simpson

[57] ABSTRACT

A shock wave source for an extracorporeal lithotripsy system has a number of electro-acoustic transducers arranged in a concave surface, each transducer having an acoustic axis, and the shock wave source having an acoustic axis. The transducers are each pivotally mounted, and a common adjusting element is provided which pivots each of the transducers so that their acoustic axes intersect at a focus, which lies on the acoustic axis of the shock wave source. The common element also permits adjustment of the location of the focus along the shock wave source acoustic axis so as to be more distal or more proximate relative to the shock wave source.

20 Claims, 2 Drawing Sheets

SHOCK WAVE SOURCE FOR EXTRACORPOREAL LITHOTRIPSY

BACKGROUND OF THE INVENTION

1. Field of the Invention

The present invention is presented to a shock wave source for use in extracorporeal lithotripsy and in particular to such a shock wave source having a plurality of electro-acoustic transducers arranged along a concave surface, which can be driven in a pulsed fashion for generating shock waves in a propagation medium disposed between the transducers and a patient.

2. Description of the Prior Art

In extracorporeal lithotripsy, a shock wave source is pressed against the body of a patient, in which a calculus is disposed, with a flexible membrane of the shock wave source functioning as a coupling agent. A suitable locating system is used to insure that the calculus to be disintegrated is located at the focus of the shock wave source. The calculus disintegrates into fragments by the action of the shock waves emanating from the shock wave source, and these fragments can be eliminated in a natural manner.

A shock wave source is described in German OS 33 19 871, corresponding to British Specification 21 40 693, wherein a plurality of electro-acoustic transducers are disposed along a concave surface. Each of the transducers can be individually driven in a pulsed manner, to generate shock waves in a propagation medium disposed between the transducers and the patient. Each transducer has an acoustic axis, and the shock wave source as a whole also has an acoustic axis. The acoustic axes of the transducers intersect at a focus which lies on the acoustic axis of the shock wave source. The transducers are arranged on a surface which is a portion of a sphere, so that the focus of the shock wave source corresponds to the center of curvature of this surface. Consequently, the transducers in this shock wave source are positioned a relatively large distance from the body surface of the patient, if the calculus to be disintegrated is disposed close to the body surface. Because this known shock wave source has a constant aperture angle, which is defined by the radius of curvature of the surface on which the transducers are arranged and by the diameter thereof, the shock waves must be coupled to the body of the patient via an extremely small region of the body surface. This results in an undesirably high power density at this location of the body surface, which may be injurious under certain circumstances.

If locating of the calculi is undertaken with an ultrasound locating system disposed in the center of the spherical surface on which the transducers are disposed, further disadvantages result. If the ultrasound locating means is disposed so that it can be applied to the body surface of the patient with only the interposition of the coupling membrane, as is most desirable for obtaining accurate ultrasound images, the ultrasound probe occupies a considerable portion of the region of the body surface available for coupling of the shock waves during treatment. This means that the power density at the remaining portion of the body surface available for treatment must be further increased in order to assure success of the treatment. If the ultrasound probe is moved away from the body surface so that an adequately large region of the body surface is available for shock wave treatment, reflections of the ultrasound waves emitted by the ultrasound probe will arise at the coupling membrane, thereby resulting in image artifacts in the ultrasound image, making locating of the calculus to be disintegrated more difficult, or impossible.

Another shock wave source is disclosed in German OS 31 19 295, corresponding to U.S. Pat. No. 4,526,168, wherein the transducers are driven with a chronologically offset signal so that the shock waves emitted from the individual transducers simultaneously arrive at the focus of the shock wave source. This known shock wave source has a control unit which acts on the drive system for the transducers, so that the chronological offset is variable and the focus of the shock wave source can thus be displaced along the acoustic axis of the shock wave source. This known shock wave source has a focal distance which is electronically variable, i.e., with electronic focusing. This permits the shock wave source to the operated with a small focal distance, and thus with a large aperture angle, for treatment of calculi lying close to the body surface of the patient, so that the power density at the body surface can be held within tolerable limits. If an ultrasound locating system is used, this can be applied to the body surface of the patient, with only the coupling membrane being interposed therebetween, at the same time as treatment, without the region of the body surface available for coupling of the shock waves being diminished due to the positioning of the ultrasound probe. In this known shock wave source, however, the extent of each transducer transversely relative to the direction of its acoustic axis cannot exceed ⅛th of the wave length of the shock wave emitted by the transducer. If this condition is not observed, excessive transit time differences will result at the focus between those components of the shock wave which are respectively emitted from the edge of the transducer and from the center of the transducer. Effective focusing would be impossible under those conditions. Consequently, this known shock wave source must have an extremely high number of relatively small transducers in order to generate shock waves having adequate energy and an adequate degree of focusing. This results in a complicated structure for the shock wave source itself, and also requires a complicated drive system and a complicated control system for the transducers. Additionally, sufficient electrical strength cannot be guaranteed, with an economic material outlay, when such extremely small transducers are used.

SUMMARY OF THE INVENTION

It is an object of the present invention to provide a shock wave source having a plurality of electro-acoustic transducers, which achieves a lower power density at the body surface of the patient being treated, for treatment of calculi lying close to the body surface, and having a simple structure and the ability to withstand the high electrical and mechanical stresses which occur during such treatment.

The above object is achieved in accordance with the principles of the present invention in a shock wave source wherein the transducers are individually pivotally mounted so that the acoustic axis of each transducer is pivotable in a plane containing the acoustic axis of the shock wave source, and having a control element for pivoting the transducers in common so that the focus, at which the acoustic axes of the transducers intersect, is movable along the acoustic axis of the shock wave source from a more proximate to a more distal focal distance, while maintaining the acoustic axis of the transducers aligned at the focus.

In the shock wave source disclosed herein the focus can thus be displaced between a more proximate and a more distal focal length, so that the aperture angle of the shock wave source is also adjustable. This provides the possibility of setting the focal distance, and thus the aperture angle of the shock wave source, in accordance with the requirements of a particular treatment, so that only a low power density exists at the body surface during coupling of the shock waves to the body of the patient. It is simultaneously possible to provide an ultrasound locating probe in the center of the shock wave source. A complicated structure of the shock wave source is avoided because the adjustment of the focal distance is undertaken mechanically. Thus relatively large transducers can be used, and a complex drive means and an associated control means (electronic) is not required. Because relatively large transducers can be used, these transducers will have an adequate electrical strength, without the need of special measures.

The shock wave emitted by the individual transducers will simultaneously arrive at the focus of the shock wave source when, taking the shape of the concave surface on which the transducers are disposed into consideration, a focal distance is selected wherein the transit time of the shock waves from the individual transducers to the focus is the same for all transducers, i.e., a focal distance wherein all of the transducers are disposed at the same distance from the focus of the shock wave source. A chronologically offset arrival of the shock waves from the individual transducers at the focus of the shock wave source, however, is not always undesirable, because it has been shown that successful treatment can be achieved even with such an offset.

In a further embodiment of the invention, however, the shock wave source can be provided with electronic focusing means for driving the individual transducers with chronologically offset signals so that the shock waves emanating from the individual transducers simultaneously arrive at the focus of the shock wave source. The control means for operating the drive system permits variation in the drive of the transducers, and can be adapted with the mechanical focusing structure so that the chronological offset can be matched to the respective pivoted positions of the transducers. Because mechanical focusing is provided in addition to this electric focusing, significantly larger transducer elements can be used than in the case of shock wave sources exclusively using electronic focusing. This permits the drive means and the control means to be constructed in a significantly less complex manner, in comparison to such systems operating exclusively by electronic focusing.

In a further embodiment of the invention, each individual transducer may be provided with a focusing element, so that each transducer emits focused shock waves. Each transducer in this embodiment has a focus, the foci coinciding on the acoustic axis of the shock wave source at a focal distance from each transducer which corresponds to the mean value of the more proximate and the more distal focal lengths of the shock wave source. This results in a focus of the shock wave source having an extremely small three-dimensional extent.

Piezo-electric transducers are preferably used as the electro-acoustic transducers in the shock wave disclosed herein.

In a further embodiment of the invention, the transducer may be combined in groups, each group containing a plurality of transducers which are arranged in an annulus, having a center axis corresponding to the acoustic axis of the shock wave source. This provides the advantage that the transit time of the shock waves emanating from each of the transducers in a group to the focus of the shock wave source is the same. If electronic focusing of the shock wave source is provided in this embodiment, the structure (circuitry) of the drive means and the control means is further simplified, since the transducers in a group can be driven in common simultaneously. Moreover, the arrangement of the transducers in groups enables a simplified structure of the mechanical pivoting elements, because all of the transducers in a group will assume the same pivoted position with respect to the acoustic axis of the shock wave source.

A simple structural arrangement of the shock wave source is achieved in an embodiment of the invention wherein the transducers are all mounted on a common holder, each transducer being pivotable around an axis disposed at a right angle relative to the plane containing the acoustic axis of that transducer and the acoustic axis of the shock wave source.

In a further embodiment of the invention, the means for pivoting the individual transducers includes a plurality of levers corresponding in number to the number of transducers, and an actuation element for the levers. Each lever has one end connected rigidly to a transducer, and an opposite end engaging the actuation element. The actuation element acts on the levers to displace the levers and pivot the transducers. If the transducers are combined in groups, the pivoting means can be further simplified by providing one actuation element for each group of transducers, this actuation element engaging the respective levers attached to all of the transducers of a group. A further structural simplification is achieved in the use of a common means for operating each of the actuation elements.

In a further embodiment of the invention, an ultrasound locating system for identifying the position of the calculus to be disintegrated is disposed in the center of the concave surface of which the transducers are disposed.

For increasing the ability of the shock wave source, to withstand electrical and mechanical stresses the shock source wave may be provided with an elastically resilient separating membrane disposed between the propagation medium and the transducers, with the transducers having their respective shock wave-emitting surfaces disposed against this membrane. The transducers may then be surrounded by an electrically insulating fluid, which does not mix with the propagation medium due to the presence of the separation membrane.

DESCRIPTION OF THE PREFERRED EMBODIMENTS

Figure 1:
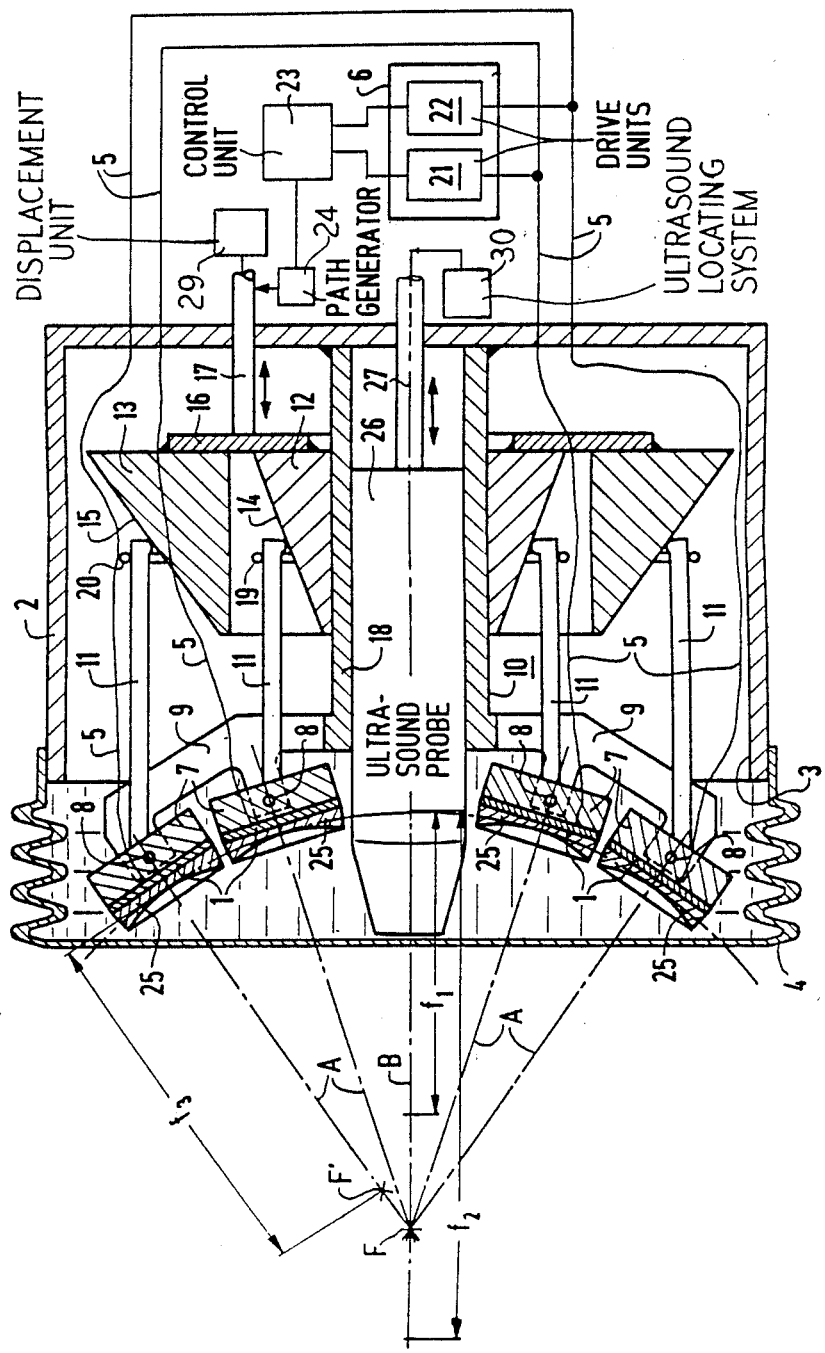
FIG. 1 is a longitudinal sectional view of a shock wave source constructed in accordance with the principles of the present invention.

As shown in the drawings, a shock wave source constructed in accordance with the principles of the present invention includes a plurality of piezo-electric transducers 1 arranged on a concave, dynamically balanced surface. This surface is shown planar (i.e., without distortion) in FIG. 2 for clarity. The surface is a portion of a sphere, as indicated with dot-dash lines in FIG. 1. The piezo-electric transducers 1 are contained in a housing 2, having an exit aperture 3 for the shock wave generated by the transducers 1. The exit aperture 3 is closed by a flexible membrane 4. The volume bounded by the housing 2 and the membrane 4 is filled with a fluid, for example water, as a propagation medium for the shock waves. During treatment of a calculus in a patient the membrane 4 is pressed against the patient, and acoustically couples the shock wave source to the patient.

Each transducer 1 has an acoustic axis A, along which the shock waves generated by that transducer propagate. The shock waves emitting from the transducers 1 converge at a focus F of the shock wave source, which lies on an acoustic axis B of the shock wave source. The acoustic axes A intersect at the focus F. Due to the spherical shape of the surface on which the transducers 1 are arranged, the acoustic axis B of the shock wave source corresponds to the center axis of the spherical surface.

The transducers 1 are connected to a drive system 6 (schematically indicated) via lines 5. The drive system 6 drives the transducers 1 with voltage pulses for generating shock waves.

Figure 2:
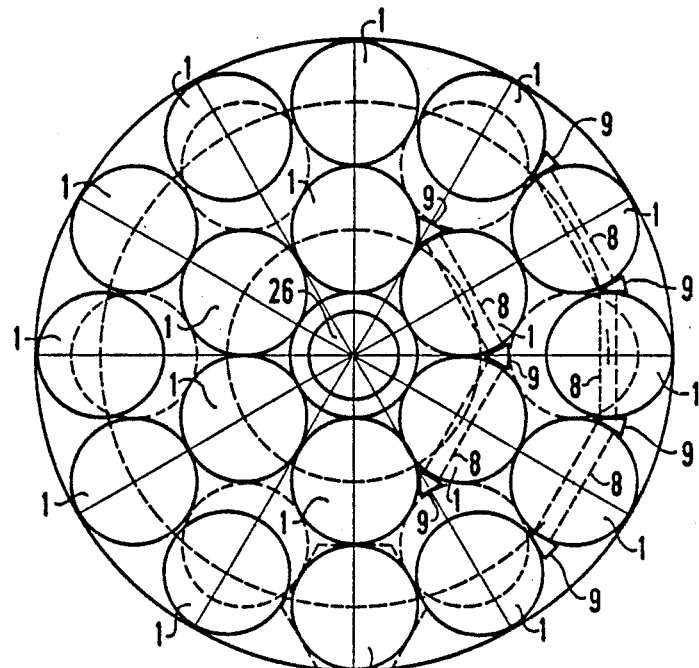
FIG. 2 is a simplified schematic front view, with the coupling membrane removed, of the shock wave source shown in FIG. 1.

Each transducer 1 has a carrier 7 by which it is pivotally mounted by a pin 8 to spaced arms 9 of a common holder 10. The holder 10 is connected to the housing 2. The transducers may be arranged or combined into two groups. The transducers 1 in each group are arranged in the form of an annulus, with the inner group containing six transducers 1 and the outer group containing twelve transducers 1, as shown in FIG. 2. The transducers in each group have the same dimensions, and the center axis of each annulus corresponds to the acoustical axis B of the shock wave source.

Each transducer 1 has a lever 11 associated therewith. One end of each lever 11 is connected to the carrier of the associated transducer 1. The opposite end of each lever 11 in a respective group of transducers 1 engages an annular control element 12 or 13, respectively associated with the inner or outer group of transducers 1. Each of the control elements 12 and 13 has a conical engagement surface 14 or 15, on which the opposite ends of the levers 11 reside. The center axes of the engagement surfaces 14 and 15 correspond to the acoustic B of the shock wave source. The control elements 12 and 13 are rigidly connected to each other by a coupler 16. A rod 17 is attached to the coupler 16, and is conducted to the exterior of the shock wave source through a wall of the housing 2 in, liquid-tight fashion and engages a schematically indicated displacement unit 29. The rod 17 is longitudinally displaceable by the unit 29, with the longitudinal axis of the rod 17 being parallel to the acoustic axis B of the shock wave source. The inner control element 12 has bore which receives a tubular projection 18 of the holder 10, and along which the control elements 12 and 13 are longitudinally displaceable. By actuating the rod 17, the control elements 12 and 13 are displaced in the direction of the acoustic axis B of the shock wave source. The respective engagement surfaces 14 and 15 of the control elements 12 and 13 thereby interact with the ends of the levers 11. The surfaces 14 and 15 are maintained in engagement with the ends of the levers 11 by annular rubber springs or riders 19 and 20, which ride on the respective surfaces 14 and 15. The interaction of the engagement surfaces 14 and 15 with the levers 11 pivots all of the transducers 1 in common, with the transducers in each group being pivoted by different amounts due to the differently inclined surfaces 14 and 15.

Each transducer 1 pivots around an axis by means of the pin 8, this axis being disposed at a right angle with respect to a plane containing the acoustic axis of the respective transducer 1, and the acoustic B of the shock wave source. The acoustic axis A of each transducer 1 is thus pivotable in a plane which contains the acoustic axis B of the shock waver source. As shown in FIG. 1, the levers 11 are attached to the associated transducers 1 so that the acoustic axes A of the all of the transducers 1, as stated above, intersect at the focus F of the shock wave source. The conical angles of the engagement surfaces 14 and 15 of the control elements 12 and 13 are selected such that the acoustic axes A of the transducers 1 intersect in a focus F on the acoustic axis B of the shock wave source for every position of the control elements 12 and 13 which can be obtained by the rod 17. The focus F is thus adjustable with infinite variation along the acoustic axis B of the shock wave source between a more proximal focal length $f_1$ and a more distal focal length $f_2$ of the shock wave source.

The drive system 6 includes two drive units 21 and 22, the drive unit 21 driving the transducers 1 of the inner group, and the drive unit 22 driving the transducers 1 of the outer group. Because the shock waves from the transducers 1 of the inner and outer groups respectively cover paths of different lengths to the focus F, depending upon the selected focal length, a control unit 23 is provided, which is connected to the drive units 21 and 22, and which is supplied with the output signal of a schematically indicated path generator 24, connected to the rod 17. The output signal of the path generator 24 represents a measure for the selected focal length on the basis on which the control unit 23 actuates the drive units 21 and 22 with a chronological offset, such that the shock waves emitted from the transducers 1 of the two groups simultaneously arrive at the selected focus F of the shock wave source. Because the transducers of a group are set at the same distance from the focus F of the shock wave source, only two drive units 21 and 22 are required.

As can be seen in FIG. 1, each transducer 1 may be provided with an acoustic lens 25 so that it emits focussed shock waves. All of the acoustic lens 25 have the same focal length $f_3$, which is selected to correspond to the mean value of the more proximal and the more distal focal lengths $f_1$ and $f_2$ of the shock wave source. This is schematically shown in FIG. 1 with the focus F' and the focal length $f_3$ being shown for a transducer 1. As a consequence of the focussed shock waves emitted by the transducers 1, the shock wave source will have a focal zone which is tightly spatially limited.

As can be seen in FIG. 2, the individual transducers 1 may each be in the shape of a circular disk. As shown with dashed lines for one of the transducers 1, the transducers may alternatively have a hexagonal shape, which permits a large emitting area to be achieved, given the same area of the spherical surface. The transducer groups may be defined by annuli of different radii, with all transducers in a group being disposed on the same annulus. If the acoustic axis A of every other transducer 1 of the outer group is disposed in the same plane as the acoustic axis of the transducer 1 adjacent thereto in the inner group, as shown in FIG. 2, it is also possible to radially displace the remaining transducers of the outer group inwardly, as shown in dashed lines in FIG. 2. The transducers 1 which are radially offset inwardly then form a third group, which must be driven with a further chronological offset using an additional drive unit (not shown) within the drive system 6.

An ultrasound locating probe 26, which is a part of an ultrasound locating system 30 for identifying the position of the calculus to be disintegrated, may be arranged in the center of the spherical surface, the focus F of the shock wave source being aligned with the calculus by means of the probe 26, and its associated ultrasound locating system. The ultrasound probe 26 is received in the tubular projection 18 of the holder 10, and thus extends along the acoustic axis B of the shock wave source. The probe 26 is longitudinally displaceable in the bore of the projection 18, so that after the shock wave source has been applied to the body of the patient to be treated, the probe 26 can be brought to a position against the body surface of the patient, with only the membrane 4 being interposed therebetween. For displacing the probe 26, a slide 27 is attached thereto, which is conducted to the exterior of the shock wave source through the housing 2 in liquid-tight fashion. The slide 27 is longitudinally displaceable as indicated by the double arrow. Electrical lines (not shown) connecting the probe 26 to the remainder of the ultrasound locating system (not shown) may be located in the interior of the slide 27.

After alignment of the focus F of the shock wave source has been undertaken using the ultrasound locating system, a further adjustment can be undertaken by using the piezo-electric transducers 1 to receive a trial shock wave reflected from the calculus to be disintegrated. The received, reflected shock waves can then be analyzed in terms of amplitude. The focal length of the shock wave source can then be further adjusted by displacing the rod 17 so that the reflected components of the shock waves have a maximum amplitude, indicating that the focal length is optimally set for this particular treatment. Using this optimization for setting the focal length, shock waves having a reduced amplitude than would otherwise be used can be emitted by the shock wave source.

Figure 3:
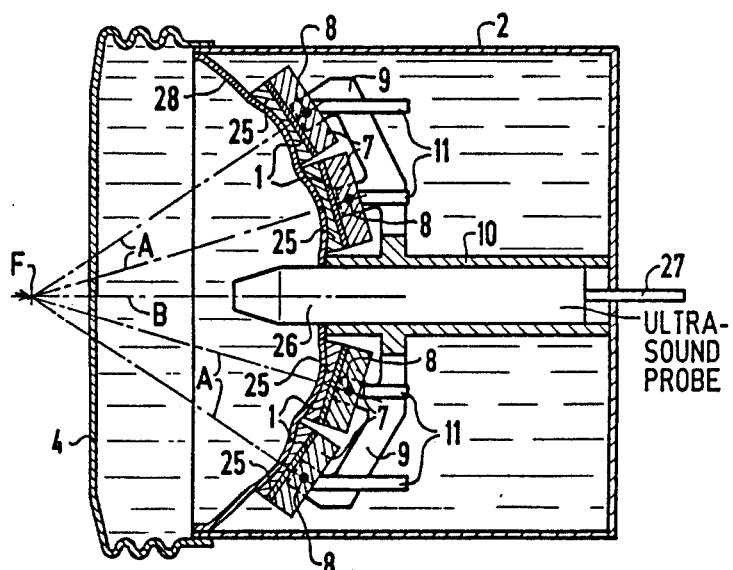
FIG. 3 is a simplified longitudinal sectional view of a further embodiment of a shock wave source constructed in accordance with the principles of the present invention.

In the embodiment shown in FIG. 3 wherein components identical to those already discussed are provided with the same reference numerals, an elastically resilient separating membrane 28 is provided between the coupling membrane 4 and the transducers 1. The outer edge of the separating membrane 28 is secured to the inside wall of the housing 2, and its inner edge is secured to the tubular projection 18 of the holder 10, both edges being secured in liquid-tight fashion, for example by gluing. The volume bounded by the housing 2 and the coupling membrane 4 is thus subdivided into two volumes by the separating membrane 28 and by the projection 18 of the holder 10. The volume between the coupling membrane 4 and the separating membrane 28 is filled with a fluid, for example, water, serving as a propagation medium for the shock waves. The remaining volume, in which the transducers 1 are disposed, is filled with an electrically insulating fluid, for example insulating oil so that an electrically and mechanically durable shock wave source is achieved.

To insure introduction of the shock waves emitted from the transducers 1 into the propagation medium via the separating membrane 28 with optimally low losses, the surface of each transducer 1 from which the shock waves are emitted is applied snugly against the separating membrane 28. In the embodiment shown in FIG. 3, these surfaces are the outer surfaces of the respective acoustic lenses 25 which face toward the focus F of the shock wave source. To insure that no spaces are present between the separating membrane 28 and the shock wave-emitting surfaces of the transducers 1, even when the transducers 1 are pivoted, the shock wave-emitting surfaces of the transducers 1 may be glued to the separating membrane 28. Alternatively, if the separating membrane 28 exhibits the necessary elasticity, as well as a suitable shaping, gluing can be omitted. It is also possible to seat the separating membrane 28 against the shock wave-emitting surfaces of the transducers 1 by generating a higher liquid pressure in the volume containing the propagation medium than in the volume containing the transducers 1.

To further avoid acoustic losses, the separating membrane 28 consists of a material having an acoustic impedance substantially corresponding to that of the propagation medium. If water is used as the propagation medium, a suitable material for the separating membrane 28 is EPDM rubber.

The remaining details of the embodiment shown in FIG. 3 correspond in structure and operation to the embodiment of FIG. 1 already described.

Although modifications and changes may be suggested by those skilled in the art, it is the intention of the inventor to embody within the patent warranted hereon all changes and modifications as reasonably and properly come within the scope of his contribution to the art.

I claim as my invention:

1. A shock wave source for non-contacting disintegration of calculi in a patient comprising:
   a housing having an emission face;
   a transducer arrangement in said housing consisting of a plurality of electro-acoustic transducers arranged on a concave surface, said transducer arrangement having an acoustic axis and each transducer having an acoustic axis in respective planes containing the acoustic axis of the transducer arrangement;
   a shock wave-propagating medium disposed in said housing at least between said transducers and said emission face;
   means for driving said transducers to generate shock waves in said medium adapted for disintegrating a calculus in a patient;
   means for individually pivotally mounting each of said transducers so that the respective acoustic axes of said transducers are pivotable in said respective planes containing the acoustic axis of the transducer arrangement; and
   means for adjustably controlling pivoting of said transducers in common so that their acoustic axes intersect at a focus on said acoustic axis of said transducer arrangement and for displacing said focus along said acoustic axis of said transducer arrangement.

2. A shock wave source as claimed in claim 1, wherein at least some transducers in said plurality of transducers are disposed at a different distance from said focus than other transducers in said plurality of transducers, and wherein said means for driving said transducers is a means for driving said transducers with chronologically offset signals so that shock waves emitting from each transducer arrive simultaneously at said focus, and further comprising means connected to said means for adjustably controlling pivoting of said transducers and to said means for driving for varying said chronological offset dependent upon the amount of pivoting of said transducers by said means for adjustably controlling pivoting.

3. A shock wave source as claimed in claim 1, wherein said focus is displaceable along said acoustic axis of said transducer arrangement by said means for adjustably controlling pivoting of said transducers between a more proximal focus and a more distal focus, and further comprising:

means associated with each transducer for focusing the shock waves generated by the associated transducer to a transducer focus on the acoustic axis of the associated transducer, said transducer focus having a focal length from said associated transducer equal to the means value of said more proximal focus and said more distal focus.

4. A shock wave source as claimed in claim 1, wherein said transducers are piezo-electric transducers.

5. A shock wave source as claimed in claim 1, wherein said plurality of transducers are arranged in a plurality of groups of transducers, each group of transducers being in the form of an annulus having a center axis coinciding with to said acoustic axis of said transducer arrangement.

6. A shock wave source as claimed in claim 1, wherein said means for individually pivotally mounting each of said transducers includes a common holder having a plurality of transducer mounts, each transducer mount having a pivot axis about which the transducer mounted-thereon pivots, said pivot axis being disposed at a right angle to the respective plane containing said acoustic axis of the transducer mounted thereon and the acoustic axis of the transducer arrangement.

7. A shock wave source as claimed in claim 1, wherein said means for adjustably controlling pivoting of said transducers comprises:

a plurality of levers equal in number to said plurality of transducers and each having a first end respectively connected to one of said transducers, and each lever having a second, opposite end;

at least one actuation element having a surface engaging said second end of said levers, said surface being disposed such that displacement of said actuation element moves said levers and pivots said transducers; and means for displacing said actuation element.

8. A shock wave source as claimed in claim 7, wherein said means for displacing said actuation element is a means for displacing said actuation element along said acoustic axis of said transducer arrangement.

9. A shock wave source as claimed in claim 7, wherein said surface of said actuation element is a portion of a conical surface.

10. A shock wave source as claimed in claim 1, wherein said plurality of electro-acoustic transducers are arranged in a plurality of groups of transducers, and wherein said means for adjustably controlling pivoting of said transducers comprises:

a plurality of sets of levers, the levers being equal in number to the plurality of transducers, the levers in each set each having a first end respectively connected to one of the transducers in a group, and having a second opposite end;

a plurality of actuation elements corresponding in number to the plurality of groups of transducers, each actuation element having a surface engaging said opposite ends of the levers in a set, each surface of each actuation element being disposed such that upon displacement of said actuation element said levers are moved and pivot the transducers in the group associated with the set of levers; and means for displacing said actuation elements.

11. A shock wave source as claimed in claim 10, wherein said means for displacing said actuation elements is a means for displacing said actuation elements in common.

12. A shock wave source as claimed in claim 10, wherein said surfaces of said actuation elements are respectively portions of differently inclined conical surfaces.

13. A shock wave source as claimed in claim 10, wherein said means for displacing said actuation elements is a means for displacing said actuation elements along said acoustic axis of said transducer arrangement.

14. A shock wave source as claimed in claim 1, further comprising means for ultrasonically locating said calculus including a probe disposed in the center of said concave surface on which said transducers are arranged.

15. A shock wave source as claimed in claim 1, further comprising:

a separating membrane disposed in said housing and dividing said housing into a first volume containing said propagation medium and a second volume containing said transducers; and an electrically insulating fluid filling said second volume.

16. A shock wave source as claimed in claim 15, wherein each transducer has a shock wave-emitting surface, and wherein said transducers are disposed with each shock wave-emitting surface against said separating membrane.

17. A shock wave source for non-contacting disintegration of calculi in a patient comprising:

a housing having an emission face;

a plurality of electro-acoustic transducers arranged in groups in said housing, each transducer having an acoustic axis, said groups being arranged non-overlapping on a spherical surface with each group forming an annulus so that each group has an acoustic axis with the respective acoustic axes of said groups coinciding with a main acoustic axis;

a propagation medium disposed in said housing at least between said transducers and said emission face;

means for driving said transducers to generate shock waves in said medium adapted for disintegrating a calculus in a patient;

means for individually pivotally mounting each of said transducers so that the respective acoustic axes of said transducers are pivotable in respective planes containing the main acoustic axis; and means for adjustably controlling pivoting of said transducers in common including a mechanical control element for each group of transducers, the respective control elements for the groups of transducers operating in common so that the acoustic axes of the transducers in said groups of said transducers intersect on said main acoustic axis at a focus and for displacing said focus along said main acoustic axis.

18. A shock wave source as claimed in claim 17, wherein said means for driving said transducers includes a plurality of drive units respectively electrically connected to said transducers in said groups of transducers, wherein said means for adjustably controlling pivoting of said transducers includes means for measuring the degree of pivoting, and wherein said means for driving said transducers further includes means for controlling said drive units, connected to said means for measuring the degree of pivoting, for operating said drive units with a chronological offset so that the shock waves generated by each of said transducers simultaneously arrive at said focus.

19. A shock wave source for non-contacting disintegration of calculi in a patient comprising:

a housing having an emission face;

a plurality of electro-acoustic transducers arranged in groups in said housing, each transducer having an acoustic axis, said groups being arranged non-overlapping on a spherical surface with each group forming an annulus so that each group has an acoustic axis with the respective acoustic axes of said groups coinciding with a main acoustic axis;

a propagation medium disposed in said housing at least between said transducers and said emission face;

plurality of drive units equal in number to the plurality of groups of transducers and respectively connected to the transducers in said groups of transducers for driving said transducers to generate shock waves in said medium adapted for disintegrating a calculus in a patient;

means for individually pivotally mounting each of said transducers so that the acoustic axis of each transducer is pivotable in one of a plurality of planes containing the main acoustic axis, said means for pivoting including a plurality of levers respectively engaging said transducers, each lever having a free end;

a plurality of commonly displaceable adjustment elements respectively associated with said groups of transducers, each adjustment element having a surface engaging the free ends of the levers attached to the transducers in the group of transducers associated therewith, and each adjustment element having a differently inclined surface engaging said levers attached to the transducers in a group so that said groups of transducers are respectively pivoted by different amounts by said adjustment elements so that the respective acoustic axes of said transducers intersect at a focus on said main acoustic axis and so that said focus is displaced along said main acoustic axis;

means for measuring the amount of pivoting of said transducers; and means connected to said means for measuring and to said drive units for controlling said drive units with a chronological offset corresponding to said amount of pivoting of said transducers so that the shock waves generated by each transducer simultaneously arrive at said focus.

20. A shock wave source as claimed in claim 19, wherein the surface of each adjustment element is a portion of a conical surface.

* * * * *